United States Patent
Kamohara et al.

(10) Patent No.: US 6,559,200 B1
(45) Date of Patent: May 6, 2003

(54) DENTAL ALGINATE IMPRESSION MATERIAL COMPOSITION

(75) Inventors: Hiroshi Kamohara, Tokyo (JP); Nobutaka Watanabe, Tokyo (JP); Makiko Takeo, Tokyo (JP); Hiroki Naito, Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 10/164,632

(22) Filed: Jun. 10, 2002

(30) Foreign Application Priority Data

Dec. 25, 2001 (JP) .......... 2001-391026

(51) Int. Cl.$^7$ .......... A61K 6/10
(52) U.S. Cl. .......... 523/109
(58) Field of Search .......... 523/109

(56) References Cited

U.S. PATENT DOCUMENTS

| | | |
|---|---|---|
| 2,678,280 A | 5/1954 | Noyes et al. |
| 2,816,843 A | 12/1957 | Erickson |
| 5,415,544 A * | 5/1995 | Oxman et al. .......... 433/48 |
| 6,335,385 B2 * | 1/2002 | Gorlich et al. .......... 523/115 |

FOREIGN PATENT DOCUMENTS

| | | |
|---|---|---|
| AU | 461 693 | 5/1975 |
| GB | 776501 | 6/1957 |
| GB | 1044160 | 9/1966 |

* cited by examiner

*Primary Examiner*—Kriellion A. Sanders
(74) *Attorney, Agent, or Firm*—Oblon, Spivak, McClelland, Maier & Neustadt, P.C.

(57) ABSTRACT

To provide a dental alginate impression material composition without the defects of the conventional alginate impression material compositions using a pH indicator, that the confirmation of the completion of the gelation is inaccurate and difficult, and that they are poor in the affinity with water to be used during the mixing, the dental alginate impression material composition containing an alginate, a gelling reaction material, a gelling adjustment material, and a filler as major components further contains 0.001 to 0.1% by weight of one or more pH indicators selected from Cresol Red, α-naphtholphthalein, Tropaeolin OOO, Thymol Blue, and phenolphthalein; 0.1 to 10% by weight of a water-soluble polyether that is a liquid at 25 ° C.; and 0.001 to 5% by weight of an inorganic pigment and/or an organic pigment having a color distinctly different from a color tone caused by color formation of the pH indicator during the gelation upon mixing with water.

2 Claims, No Drawings

DENTAL ALGINATE IMPRESSION MATERIAL COMPOSITION

BACKGROUND OF THE INVENTION

1. Field of the Invention:

The present invention relates to a dental alginate impression material composition to be used for taking an impression in the oral cavity in the dentistry. In particular, the present invention relates to a dental alginate impression material that produces a distinct change in color tone before and after the gelation upon mixing with water and has good affinity with water to be used for mixing.

2. Description of the Related Art:

In the dentistry, a dental alginate impression material composition is widely used as an impression material for taking an impression in the oral cavity during the preparation of a prosthesis. This dental alginate impression material composition contains an alginate, a gelling reaction material, a gelling adjustment material, and a filler as major components and when mixed with water, is set in a gel form. The dental alginate impression material composition is usually provided in the form of a powder, and the powder is mixed with a predetermined amount of water to form a paste, which is then inserted into the oral cavity and set.

In the dental alginate impression material composition, since it is used upon being gelled within the oral cavity, whether or not the composition has been actually gelled so that it can be taken out from the oral cavity is determined by following an intraoral holding time instructed by a maker, or by a method in which an operator confirms whether or not it has been gelled and set by pressing the impression material within the oral cavity by fingers. However, since the degree of gelation is likely influenced by the atmospheric temperature or water temperature, in many cases, the dental alginate impression material composition is not gelled within the intraoral holding time instructed by the maker depending on the working environment, and thus there was a defect that the impression became incomplete in such cases. Further, in the method in which the operator determines the gelation by fingers, a difference is large depending on the operator, which causes the impression to be incomplete.

In order to overcome these inconveniences, impression materials of a type that they produce a distinct change in color tone before and after the gelation upon mixing with water are on the market. In these conventional alginate impression material compositions, the change in color tone is effected by a method as described later. That is, in general alginate impression materials, while the pH immediately after the mixing is slightly higher than 8, the pH is lowered according to the progress of the gelation, and the pH becomes lower than 8 when the gelation is completed. Thus, in the conventional alginate impression material compositions which change the color tone, by utilizing this phenomenon, a pH indicator that distinctly forms a color at the pH before the gelation is contained, and by utilizing the pH change after the gelation, the completion of the gelation is visually confirmed when the pH indicator does not distinctly form a color.

However, actually, the change in color tone occurs at a considerably early stage before the gelation due to influences of various salts contained in the alginate impression material composition, so that there is no reliable standard for determining the completion of the gelation. Accordingly, these conventional alginate impression material compositions are scarcely employed at present. Further, the pH indicator is poor in the affinity with water to be used during the mixing. Accordingly, the pH indicator was very difficult to be employed from the standpoint of the mixing operation.

SUMMARY OF THE INVENTION

The present invention is aimed to provide a dental alginate impression material composition that can overcome the defects of the conventional alginate impression material compositions using a pH indicator, i e., the defect that the confirmation of the completion of the gelation is inaccurate and difficult, and the defect that they are poor in the affinity with water to be used during the mixing.

In order to achieve the above described aim, we, the present inventors made extensive and intensive investigations. As a result, it has been found that when a specified pH indicator is compounded in a dental alginate impression material composition, and a specified water-soluble polyether is simultaneously added to the composition, even the dental alginate impression material composition having the pH indicator compounded therein has good affinity with water, and it is possible to prevent the pH indicator from the occurrence of a change from an early stage; and further that when an inorganic pigment and/or an organic pigment having a color distinctly different from a color tone expressed by the color formation of the pH indicator caused during the gelation upon mixing with water is co-present in the composition, it is possible to make the change of pH indicator coincident with the gelation, leading to the accomplishment of the present invention.

Specifically, the present invention is concerned with a dental alginate impression material composition containing an alginate, a gelling reaction material, a gelling adjustment material, and a filler as major components, which comprises 0.001 to 0.1% by weight of one or more pH indicators selected from Cresol Red, α-naphtholphthalein, Tropaeolin OOO, Thymol Blue, and phenolphthalein; 0.1 to 10% by weight of a water-soluble polyether that is a liquid at 25° C.; and 0.001 to 5% by weight of an inorganic pigment and/or an organic pigment having a color distinctly different from a color tone expressed by color formation of the pH indicator caused during the gelation upon mixing with water.

DETAILED DESCRIPTION OF THE INVENTION

In the dental alginate impression material composition containing an alginate, a gelling reaction material, a gelling adjustment material, and a filler as major components, which is used in the present invention, as the alginate, can be used one or more water-soluble salts of alginic acid with, for example, sodium, potassium, ammonium, triethanolamine, etc. The alginate is contained in an amount of 10 to 20% by weight, as in the usual alginate impression material compositions. As the gelling reaction material, can be used sparingly soluble salts of a metal having a valence of two or more, and preferably a dihydrate or hemihydrate of calcium sulfate. As the gelling adjustment material, can be used one or more phosphates, silicates, carbonates, etc. of sodium or potassium. As the filler, can be used one or more powders such as diatomaceous earth, silicic anhydride, talc, calcium carbonate, and perlite. In order to impart the characteristics of the present invention, the components as described later are compounded in such a conventional dental alginate impression material composition containing an alginate, a gelling reaction material, a gelling adjustment material, and a filler as major components.

The specified pH indicator that is used in the present invention is at least one pH indicator selected from Cresol Red, α-naphtholphthalein, Tropaeolin OOO, Thymol Blue, and phenolphthalein. These pH indicators are pH indicators capable of forming a distinct color in a pH region slightly higher than pH 8, which is the pH value at the time of the completion of mixing of the dental alginate impression material composition. A method for confirming the progress of the gelation utilizing the pH indicator is a technology that has hitherto been employed. However, according to the change in color tone only by the pH indicator, there are involved problems that the color expressed by the change in color tone becomes indistinct before the completion of the gelation and that the change in color tone occurs due to other salts contained in the composition even before the gelation, as described above. Accordingly, the present invention makes it possible to determine the occurrence of the gelation accurately and with a distinct color, when the water-soluble polyether that is a liquid at 25° C. and the inorganic pigment and/or organic pigment as described later are co-present in the dental alginate impression material composition.

The at least one pH indicator selected from Cresol Red, α-naphtholphthalein, Tropaeolin OOO, Thymol Blue, and phenolphthalein is contained in an amount of 0.001 to 0.1% by weight in the alginate impression material. When the amount of the ph indicator is less than 0.001% by weight, the color formation necessary for the accurate determination is not obtained, whereas when it exceeds 0.1% by weight, the discrimination of the color after the gelation becomes inaccurate.

Examples of the water-soluble polyether that is a liquid at 25° C. to be used in the present invention include polyethylene glycol, polypropylene glycol, and polyethylene glycol-polypropylene glycol. These specified polyethers have an effect for preventing the pH indicator from the change in color tone due to other salts and the like contained in the alginate impression material composition at an early stage before the completion of the gelation. Further, since these specified polyethers are soluble in water, when used during the mixing, even the dental alginate impression material composition containing the specified pH indicator as described above is extremely good in affinity with water. The water-soluble polyether that is a liquid at 25° C. is contained in an amount of 0.1 to 10% by weight in the dental alginate impression material composition. When the amount of the water-soluble polyether that is a liquid at 25° C. is less than 0.1% by weight, satisfactory effects cannot be obtained, whereas when it exceeds 10% by weight, the stability during the preservation of the composition and the surface properties of a plaster model as prepared by pouring gypsum into the set impression material are poor.

The inorganic pigment and/or organic pigment that is used in the present invention exhibits the effect when used in combination with the specified pH indicator as described above. Specifically, as described above, the pH indicator that is used in the present invention forms a color in a pH region slightly higher than pH 8 which is the pH value immediately after mixing with water. The pH is lowered, as the gelation progresses, and the pH indicator does not substantially form a color at the pH at the time of the completion of the gelation. For this reason, the color tone immediately after the mixing is a combination of the color of the pH indicator and that of the pigment, whereas the color tone at the time of the completion of the gelation is the color only by the pigment because the pH indicator does not form a color. That is, in the conventional alginate impression materials, the color tone that they initially exhibit becomes pale as the gelation progresses, whereas in the dental alginate impression material composition according to the present invention, the color tone changes to the color tone of the pigment which is different from that of the pH indicator at the initial stage, so that the confirmation of the change in color tone is quite distinct.

As the pigment that is used in the present invention, employable are any inorganic pigments and organic pigments. Also, the both may be used in combination. The pigment must have a color clearly different from the color tone exhibited by the pH indicator at the time of the completion of the mixing. For example, since α-naphtholphthalein as the pH indicator to be used in the present invention forms a blue color at the time of start of the mixing of the alginate impression material, it is preferably colored to a color tone different from the blue color with, for example, a yellow pigment (such as titanium yellow and condensed azo yellow pigments) or a red pigment (such as red oxide and condensed azo red pigments). The inorganic pigment and/or organic pigment is contained in an amount of 0.001 to 5% by weight in the dental alginate impression material composition. When the amount of the inorganic pigment and/or organic pigment is less than 0.001% by weight, the color is not distinct, whereas when it exceeds 5% by weight, the color formation by the pH indicator is negated, and as a result, the discrimination of the change in color tone before and after the gelation is difficult.

As a matter of course, the dental alginate impression material composition according to the present invention may further contain various disinfectants, perfumes, and the like so far as the characteristics of the dental alginate impression material composition are not impaired.

Next, the present invention will be described in detail with reference to the following. Examples, but it should not be construed that the present invention is limited thereto.

EXAMPLE 1

Basic formulation of dental alginate impression material composition

| | |
|---|---|
| Sodium alginate: | 15% by weight |
| Calcium sulfate dihydrate: | 15% by weight |
| Sodium triphosphate: | 0.8% by weight |
| Sodium carbonate: | 0.2% by weight |
| Diatomaceous earth: | 68.898% by weight |
| Specified water-soluble polyether | |
| Polyethylene glycol | 0.1% by weight |
| Specified pH indicator | |
| α-Naphtholphthalein: | 0.001% by weight |
| Inorganic pigment and/or organic pigment | |
| Chromophthal Red (condensed azo pigment) | 0.001% by weight |

The above-described components were well mixed in a blender to obtain a dental alginate impression material composition.

(Accuracy in Confirmation of Gelation Time by Discoloration)

The above-described composition (17 g) and water (40 cc) were weighed and mixed and kneaded in a dental rubber cup for 20 seconds. The mixture was charged in a mold for preparing a specimen for permanent strain test as defined in JIS T6505 and immersed in warm water at 35° C. At the time when the color tone of the specimen changed, the specimen was taken out from the mold and subjected to a permanent strain test. Next, after mixing the above-described composition in the same manner as described above, the mixture was charged in a mold for preparing a specimen for permanent strain test and immersed in warm water at 35° C. One minute after the time when the change of the color tone could be confirmed, the specimen was taken out from the mold and subjected to a permanent strain test. When a difference in the permanent strain between the both is not substantially observed, it can be determined that the gelation has been completed at the time when the color tone of the specimen has changed. The results obtained are summarized and shown in Table 1. (Affinity of dental alginate impression material composition with water)

The above-described composition (17 g) and water (40 cc) were weighed and mixed in a dental rubber cup. At this time, while taking into account the time when the above-described composition became intimate with water and could be actually started for the mixing operation as a standard, the affinity of the dental alginate impression material with water was evaluated according to two grades: "good" and "poor". The results obtained are summarized and shown in Table 1.

EXAMPLE 2

Basic formulation of dental alginate impression material composition

| | |
|---|---|
| Sodium alginate: | 14% by weight |
| Calcium sulfate dihydrate: | 15% by weight |
| Sodium triphosphate: | 0.8% by weight |
| Sodium carbonate: | 0.2 % by weight |
| Potassium fluorotitanate | 1% by weight |
| Diatomaceous earth: | 67% by weight |
| Specified water-soluble polyether | |
| Polypropylene glycol | 1% by weight |
| Specified pH indicator | |
| α-Naphtholphthalein: | 0.01% by weight |
| Inorganic pigment and/or organic pigment | |
| Titanium yellow | 0.99% by weight |

The above-described components were well mixed in a blender to obtain a dental alginate impression material composition. The thus obtained alginate impression material composition was tested in the same manner as in Example 1. The results obtained are summarized and shown in Table 1.

EXAMPLE 3

Basic formulation of dental alginate impression material composition

| | |
|---|---|
| Sodium alginate: | 15% by weight |
| Calcium sulfate dihydrate: | 15% by weight |
| Sodium triphosphate: | 0.7% by weight |
| Sodium carbonate: | 0.3% by weight |
| Potassium fluorotitanate | 1% by weight |
| Diatomaceous earth: | 57.9% by weight |
| Specified water-soluble polyether | |
| Polypropylene glycol | 5.5% by weight |
| Specified pH indicator | |
| Phenolphthalein: | 0.1% by weight |
| Inorganic pigment and/or organic pigment | |
| Cobalt blue | 4.5% by weight |

The above-described components were well mixed in a blender to obtain a dental alginate impression material composition. The thus obtained alginate impression material composition was tested in the same manner as in Example 1. The results obtained are summarized and shown in Table 1.

EXAMPLE 4

Basic formulation of dental alginate impression material composition

| | |
|---|---|
| Sodium alginate: | 15% by weight |
| Calcium sulfate dihydrate: | 15% by weight |
| Sodium triphosphate: | 0.5% by weight |
| Sodium carbonate: | 0.5% by weight |
| Potassium fluorotitanate | 1% by weight |
| Diatomaceous earth: | 66.475% by weight |
| Specified water-soluble polyether | |
| Polypropylene glycol | 1.5% by weight |
| Specified pH indicator | |
| α-Naphtholphthalein: | 0.01% by weight |
| Phenolphthalein: | 0.005% by weight |
| Inorganic pigment and/or organic pigment | |
| Chromophthal Yellow (condensed azo pigment) | 0.01% by weight |

The above-described components were well mixed in a blender to obtain a dental alginate impression material composition. The thus obtained alginate impression material composition was tested in the same manner as in Example 1. The results obtained are summarized and shown in Table 1.

COMPARATIVE EXAMPLE 1

Basic formulation of dental alginate impression material composition

| | |
|---|---|
| Sodium alginate: | 15% by weight |
| Calcium sulfate dihydrate: | 15% by weight |
| Sodium triphosphate: | 0.8% by weight |
| Sodium carbonate: | 0.2% by weight |
| Potassium fluorotitanate | 1% by weight |
| Diatomaceous earth: | 67.99% by weight |
| Specified pH indicator | |
| α-Naphtholphthalein: | 0.01% by weight |

The above-described components were well mixed in a blender to obtain a dental alginate impression material composition. The thus obtained alginate impression material composition was tested in the same manner as in Example 1. The results obtained are summarized and shown in Table 1.

COMPARATIVE EXAMPLE 2

Basic formulation of dental alginate impression material composition

| | |
|---|---|
| Sodium alginate: | 15% by weight |
| Calcium sulfate dihydrate: | 15% by weight |
| Sodium triphosphate: | 0.8% by weight |
| Sodium carbonate: | 0.2% by weight |
| Potassium fluorotitanate | 1% by weight |
| Diatomaceous earth: | 66.99% by weight |
| Specified pH indicator | |
| α-Naphtholphthalein: | 0.01% by weight |
| Specified water-soluble polyether | |
| Polypropylene glycol: | 1% by weight |

The above-described components were well mixed in a blender to obtain a dental alginate impression material composition. The thus obtained alginate impression material composition was tested in the same manner as in Example 1. The results obtained are summarized and shown in Table 1.

TABLE 1

|  | Example | | | | Comparative Example | |
| --- | --- | --- | --- | --- | --- | --- |
|  | 1 | 2 | 3 | 4 | 1 | 2 |
| Permanent strain (%) | | | | | | |
| Immediately after the occurrence of a change in color tone | 2.1 | 2.3 | 2.2 | 2.1 | 4.2 | 3.0 |
| One minute after the occurrence of a change in color tone | 2.1 | 2.3 | 2.2 | 2.1 | 2.2 | 2.2 |
| Affinity with water | Good | Good | Good | Good | Poor | Good |

It can be understood from Table 1 that in the dental alginate impression material composition according to the present invention, there is no difference in the permanent strain between the time when it was taken out immediately after the occurrence of a change in color tone and the time when it was taken out one minute after the occurrence of a change in color tone, and hence, the completion of the gelation was coincident with the time when the occurrence of a change in color tone was confirmed. On the other hand, in the composition containing only the pH indicator of Comparative Example 1, the color tone has changed at a considerably early stage before the completion of the gelation, and there was a great difference between the permanent strain immediately after the occurrence of a change in color tone and the permanent strain one minute after the occurrence of a change in color tone. Further, in Comparative Example 2, the time when the changing of the color tone was prolonged as compared with that in Comparative Example 1, and the difference between the time when the gelation was completed and the time when the changing of the color tone was small. However, since the composition of Comparative Example 2 does not contain the pigment, the determination of the occurrence of a change in color tone is not distinct, and there is still a great difference between the time when the gelation actually occurred and the time when the changing of the color tone was confirmed, leading to a problem.

As described above, the dental alginate impression material according to the present invention overcomes the defects of the conventional alginate impression material compositions using a pH indicator, i.e., the defect that the confirmation of the completion of the gelation is inaccurate and difficult, and the defect that they are poor in the affinity with water to be used during the mixing, has good affinity with water, and is able to accurately confirm the gelation time by color tone. Therefore, the present invention is greatly valuable in contributing to the dental field.

While the present invention has been described in detail and with reference to specific embodiments thereof, it will be apparent to one skilled in the art that various changes and modifications can be made therein without departing from the spirit and scope thereof.

What is claimed is:

1. A dental alginate impression material composition containing an alginate, a gelling reaction material, a gelling adjustment material, and a filler as major components, which comprises 0.001 to 0.1% by weight of one or more pH indicators selected from Cresol Red, α-naphtholphthalein, Tropaeolin 000, Thymol Blue, and phenolphthalein; 0.1 to 10% by weight of a water-soluble polyether that is a liquid at 25° C.; and 0.001 to 5% by weight of an inorganic pigment and/or an organic pigment having a color distinctly different from a color tone caused by color formation of the pH indicator during the gelation upon mixing with water.

2. The dental alginate impression material composition as claimed in claim 1, wherein the water-soluble polyether is polyethylene glycol, polypropylene glycol, or polyethylene glycol-polypropylene glycol.

* * * * *